US007790006B2

(12) United States Patent
Feng et al.

(10) Patent No.: US 7,790,006 B2
(45) Date of Patent: Sep. 7, 2010

(54) FREE CHLORINE SENSOR

(75) Inventors: Chang-Dong Feng, Long Beach, CA (US); Jishou Xu, Irvine, CA (US); Joshua Steven Garretson, Santa Barbara, CA (US)

(73) Assignee: Rosemount Analytical Inc., Irvine, CA (US)

( * ) Notice: Subject to any disclaimer, the term of this patent is extended or adjusted under 35 U.S.C. 154(b) by 1513 days.

(21) Appl. No.: 10/939,866

(22) Filed: Sep. 13, 2004

(65) Prior Publication Data

US 2005/0029103 A1 Feb. 10, 2005

Related U.S. Application Data

(63) Continuation-in-part of application No. 10/138,359, filed on May 3, 2002, now Pat. No. 7,087,150.

(51) Int. Cl.
*G01N 27/26* (2006.01)
(52) U.S. Cl. .................. 204/432; 204/415; 205/775
(58) Field of Classification Search .......... 204/415, 204/403.4, 449; 205/775; 73/23.2; 514/44
See application file for complete search history.

(56) References Cited

U.S. PATENT DOCUMENTS

| | | | |
|---|---|---|---|
| 3,429,796 A | 2/1969 | Lauer | |
| 3,708,412 A | 1/1973 | Lofgren | 204/415 |
| 3,755,125 A | 8/1973 | Shaw et al. | 204/195 |
| 3,926,764 A * | 12/1975 | Ruzicka et al. | 204/418 |
| 3,959,087 A | 5/1976 | Morrow | 204/1 T |
| 4,111,760 A | 9/1978 | Chen et al. | 204/26 |
| 4,129,479 A | 12/1978 | Morrow | 204/1 T |
| 4,176,031 A | 11/1979 | Rosenblum | 204/195 R |
| 4,201,634 A | 5/1980 | Stetter | 205/780.5 |
| 4,278,507 A | 7/1981 | Derreumaux et al. | 204/1 T |
| 4,322,215 A | 3/1982 | Huber et al. | 23/230 R |
| 4,435,268 A * | 3/1984 | Martin et al. | 204/408 |

(Continued)

FOREIGN PATENT DOCUMENTS

CA    2 360 599    5/2002

(Continued)

OTHER PUBLICATIONS

A First Communication of the European Patent Office in foreign application No. 05773329.7 filed Jul. 22, 2005.

(Continued)

*Primary Examiner*—Mark F Huff
*Assistant Examiner*—Rashid Alam
(74) *Attorney, Agent, or Firm*—Christopher R. Christenson; Westman, Champlin & Kelly, P.A.

(57) ABSTRACT

A free chlorine measurement system and sensor are provided. In accordance with one aspect of the invention, the sensor has a porous working electrode disposed in an electrolyte proximate a porous membrane. The membrane allows free chlorine therethrough where it is reduced and generates a current. The current is related to the free chlorine concentration. The internal electrolyte solution is pH stabilized with a long-term pH stabilizer that has a solubility in water at room temperature between about 1.2 moles/liter and about 0.001 moles/liter. The stabilizer can be an acid or a base depending on whether the pH is to be stabilized at a relatively low value or a relatively high value respectively.

11 Claims, 5 Drawing Sheets

U.S. PATENT DOCUMENTS

| | | | |
|---|---|---|---|
| 4,525,704 A | 6/1985 | Campbell et al. | 340/632 |
| 4,756,804 A | 7/1988 | Driscoll et al. | 204/1 |
| 4,776,942 A | 10/1988 | Neti et al. | 204/415 |
| 4,822,474 A | 4/1989 | Corrado | 204/402 |
| 5,030,336 A | 7/1991 | Koch | 204/415 |
| 5,302,274 A | 4/1994 | Tomantschger et al. | 204/412 |
| 5,693,204 A | 12/1997 | Popp | 204/409 |
| 5,711,861 A | 1/1998 | Ward et al. | 204/403 |
| 5,725,747 A | 3/1998 | Pinkowski et al. | 204/415 |
| 5,728,290 A | 3/1998 | Xie et al. | 205/783 |
| 5,770,039 A | 6/1998 | Rigney et al. | 205/789 |
| 5,830,337 A | 11/1998 | Xu | 204/400 |
| 5,841,021 A * | 11/1998 | De Castro et al. | 73/23.2 |
| 5,855,750 A | 1/1999 | Kiesele | 204/415 |
| 5,869,342 A | 2/1999 | Stannard et al. | 436/55 |
| 5,944,966 A * | 8/1999 | Suetsugu et al. | 205/150 |
| 6,200,447 B1 * | 3/2001 | Brucken et al. | 204/499 |
| 6,248,224 B1 * | 6/2001 | Kitzelmann | 204/431 |
| 6,306,284 B1 * | 10/2001 | Yang et al. | 205/778.5 |
| 6,423,209 B1 * | 7/2002 | Weber et al. | 205/775 |
| 2001/0032789 A1 | 10/2001 | Babes-Dornea et al. | |
| 2001/0052459 A1 * | 12/2001 | Essalik et al. | 204/421 |
| 2002/0036146 A1 * | 3/2002 | Akutsu et al. | 205/316 |
| 2002/0132179 A1 * | 9/2002 | Yamada et al. | 430/264 |
| 2002/0166776 A1 * | 11/2002 | Fikus et al. | 205/782 |
| 2003/0205465 A1 | 11/2003 | Feng | 204/415 |

FOREIGN PATENT DOCUMENTS

| | | |
|---|---|---|
| DE | 198 47 706 | 4/2000 |
| GB | 858677 | 1/1961 |
| GB | 1569 026 | 6/1980 |
| JP | 01 041853 | 2/1989 |

OTHER PUBLICATIONS

International Search Report and Written Opinion from application No. PCT/US2005/025830, filed Jul. 22, 2005.
"Chlorine Residual Analyzer Series 1770," Severn Trent Services, pp. 1-4 (2000).
"Chlorine Residual Analyzer Series 1870E," Severn Trent Services, pp. 1-4 (2000).
"E-TEK Catalogue, C. Noble Metal Catalysts on Carbon," downloaded from http://www.etek-inc.com/C.html, 7 pages (Aug. 14, 2001).
"E-TEK Catalogue, C. Noble Metal Catalysts on Carbon," downloaded from http://wwww.eteck-inc.com/C1-7.html, 5 pages (May 24, 2001).
"E-TEK Catalogue, A-5 Sensor Electrodes (ESE)," downloaded from http://www.etek-inc.com/A5.html, 2 pages (Aug. 14, 2001).
"E-TEK Catalogue, A-1 Carbon Cloth Electrode (ECC)," downloaded from http://www.etek-inc.com/Al.html, 2 pages (Aug. 15, 2001).
"E-TEK Catalogue, A. Gas Diffusion Electrodes & Services," downloaded from http://www.etek-inc.com/A.html, 2 pages (Aug. 14, 2001).
"Applications. What is a Gas Diffusion Electrode?" downloaded from http://www.etek-inc.com/applications.html, 3 pages (Aug. 14, 2001).
"ChemScan® UV-2150 Process Analyzers," downloaded from http://www.chemscan.com/literature/uv-2150.html, 9 pages (Sep. 13, 2001).
"ChemScan® UV-6101 Process Analyzers," downloaded from http://www.chemscan.com/literature/uv-6101.html, 4 pages (Sep. 13, 2001).
"ChemScan® Application Summary, Ammonia Feed Control (Chloramination)" downloaded from http://www.chemscan.com/applications/101.html, 2 pages (Sep. 13, 2001).
"ChemScan® Application Summary, Chlorination Control" downloaded from http://www.chemscan.com/applications/99.html, 2 pages (Sep. 13, 2001).
"ChemScan® UV-6101 Process Analyzers," downloaded from http://www.chemscan.com/literature/uv-6101.html, 4 pages (Sep. 13, 2001).
"ChemScan® UV-4100 Process Analyzers," downloaded from http://www.chemscan.com/literature/uv-4100.html, 5 pages (Sep. 13, 2001).
"ChemScan® UV-3150 Process Analyzers," downloaded from http://www.chemscan.com/literature/uv-3150.html, 5 pages (Sep. 13, 2001).
"ChemScan® Application Summary, Wastewater Chloramination Process Control" downloaded from http://www.chemscan.com/applications/82.html, 2 pages (Sep. 13, 2001).
"ChemScan® Application Summary, Water Chloramination Process Control" downloaded from http://www.chemscan.com/applications/86.html, 4 pages (Sep. 13, 2001).
"Chlormaines," Gerard J. Gash, OSMONICS, downloaded from http://www.osmonics.com/products/Page813.htm, 5 ages. (Sep. 17, 2001).
"A Closer Look At Water Treatment," HACH Company, 1 page (1997).
"Monitoring Chlormaination Using the APA6000 Ammonia/Monochloramine Analyzer," Application Note 123, 6 pages (2000).
"APA 6000 Ammonium & Nitrate Analyzer with AquaTrend Interface," HACH Company, 6 pages (1998).
"Model 1054B CL Chlorine Microprocessor Analyzer," Emerson Process Management, downloaded from http://www.rauniloc.com/1-800-854-8257/01_products_00.php?body=ch_analyzers_1054BCL, 2 pages (Feb. 15, 2002).
"Field Commissioned Dual Measured Analyzer," Emerson Process Management, downloaded from http://www.rauniloc.com/1-800-854-8257/01_products_00.php?body=analyzers_1055FC, 1 page (Feb. 15, 2002).
"Free Chlornie," Emerson Process Management, downloaded from http://www.rauniloc.com/1-800-854-8257/01_products_00.php?body=ch_transmitters_1181RC, 1 page (Feb. 15, 2002).
"Chlorine Measurement by Amperometric Sensor," Application Data, Rosemount Analytical, 1 page (Dec. 1998).
Rosemount Analytical—Uniloc Division launches their 499A TrDO (Trace Dissolved Oxygen) Sensor, 1 page (Mar. 2, 2001).
"APA 6000 Series Analyers: Overview" HACH Company, 5 pages (Sep. 12, 2001).
U.S. Appl. No. 10/138,359, filed May 2002, Feng.
First Office Action from Chinese patent application No. 200580022198.2, dated Apr. 24, 2009.
First Examiner's Report for Australian patent application No. 2005285460, dated Feb. 17, 2010.

\* cited by examiner

FREE CHLORINE SENSOR

CROSS REFERENCE TO RELATED APPLICATION

This application is a Continuation-In-Part application of U.S. patent application Ser. No. 10/138,359, filed May 3, 2002, entitled Chloramine Amperometric Sensor.

BACKGROUND OF THE INVENTION

The present invention relates to quantitative analytic sensors. More specifically the present invention relates to a sensor that uses an electrode response to measure the concentration of free chlorine in a solution.

Chlorine, in one form or another, is often used as a disinfectant for the treatment of water. Such treatment can include disinfecting drinking water, treating swimming pools, disinfecting articles that come into contact with water, and many other applications in which it is desirable to kill bacteria in water. Proper operation of water disinfectant systems generally requires the measurement of chlorine in order to ensure that a sufficient amount of chlorine has been used.

Free chlorine is chlorine in one or more forms that are useful as disinfectants. Free chlorine can exist as dissociated chlorine gas, hypochlorite ion, and hypoclorous acid. The relative ratio of hypochlorite ion to hypoclorous acid is known to be related to the pH of the solution. Rosemount Analytical Incorporated, an Emerson Process Management Company, provides a free chlorine sensor for the continuous determination of free chlorine, under the trade designation model 499ACL-01. The sensor can measure free chlorine in samples having pH as high as 9.5 and operates as an amperometric sensor.

In general, prior art free chlorine sensors needed to be paired with some form of pH compensation. Compensation of the pH was necessary because only the hypoclorous acid form of free chlorine is reducible at the cathode of an amperometric device. As set forth above, free chlorine exists in two forms in solutions: hypochlorite ion and hypoclorous acid with the relative ratio of the two being dependent upon the pH of the solution. Below pH 6, free chlorine is effectively 100% hypoclorous acid, while above pH 10, free chlorine is effectively 100% hypochlorite ion. The relative concentrations of hypochlorite ion and hypochlorous acid varying with pH as illustrated in FIG. 1.

It would be extremely useful if free chlorine sensing could be done without the additional sensing of pH. The current state of the art wherein pH must be sensed or known to some degree unnecessarily complicates free chlorine measurement and increases the expense of measurement systems.

Attempts have been made to mitigate the effects of varying pH on chlorine measurements. For example, buffers have been used in order to attempt to maintain the internal electrolyte solution at a selected pH. Further, U.S. Pat. No. 5,693,204 to Popp provides passive pH adjustment for analytical instruments. However, attempts, to date, involved cumbersome pH maintenance systems or independent pH compensation for the chlorine measurement. The provision of a free chlorine sensor that would not require pH measurement and compensation, as well as the provision of a simple and easily serviced free chlorine sensor would advance the art of free chlorine sensing and lower overall costs for providing and maintaining water disinfectant systems.

SUMMARY OF THE INVENTION

A free chlorine measurement system and sensor are provided. In accordance with one aspect of the invention, the sensor has a porous working electrode disposed in an electrolyte proximate a porous membrane. The membrane allows free chlorine therethrough where it is reduced and generates a current. The current is related to the free chlorine concentration. The internal electrolyte solution is pH stabilized with a long-term pH stabilizer that has a solubility in water at room temperature between about 1.2 moles/liter and about 0.001 moles/liter. The stabilizer can be an acid or a base depending on whether the pH is to be stabilized at a relatively low value or a relatively high value respectively.

DETAILED DESCRIPTION OF THE PREFERRED EMBODIMENTS

Embodiments of the present invention provide a free chlorine sensor with a porous cathode assembly and an acid or base disposed in the electrolyte fill solution with a solubility in a water at room temperature between about 1.2 mole/liter and about 0.001 mole/liter. This arrangement provides a useful free chlorine amperometric sensor that can operate without pH compensation.

Figure 1:
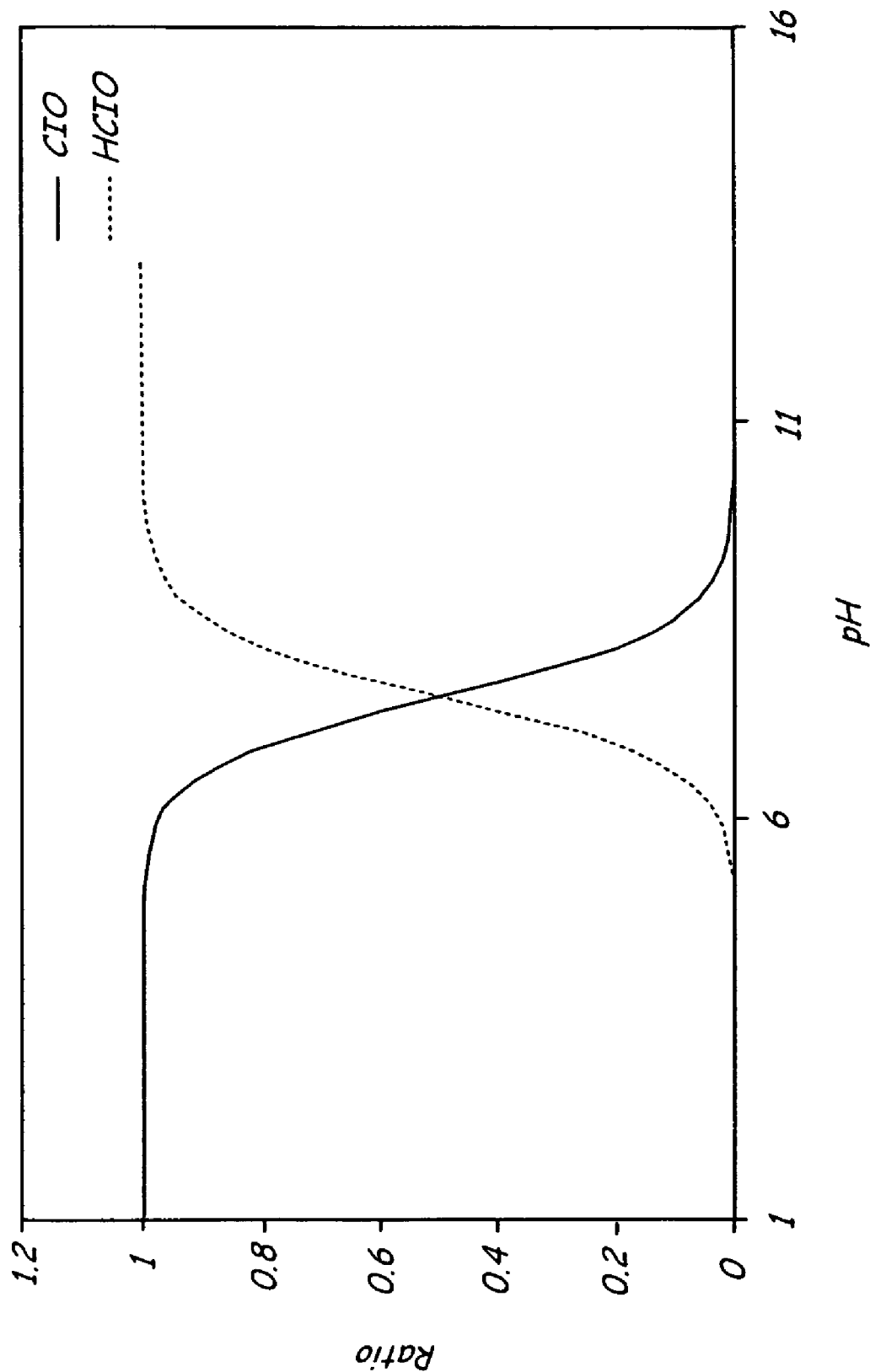
FIG. 1 is a chart of the ratio of free chlorine species as a function of pH.
Figure 2:
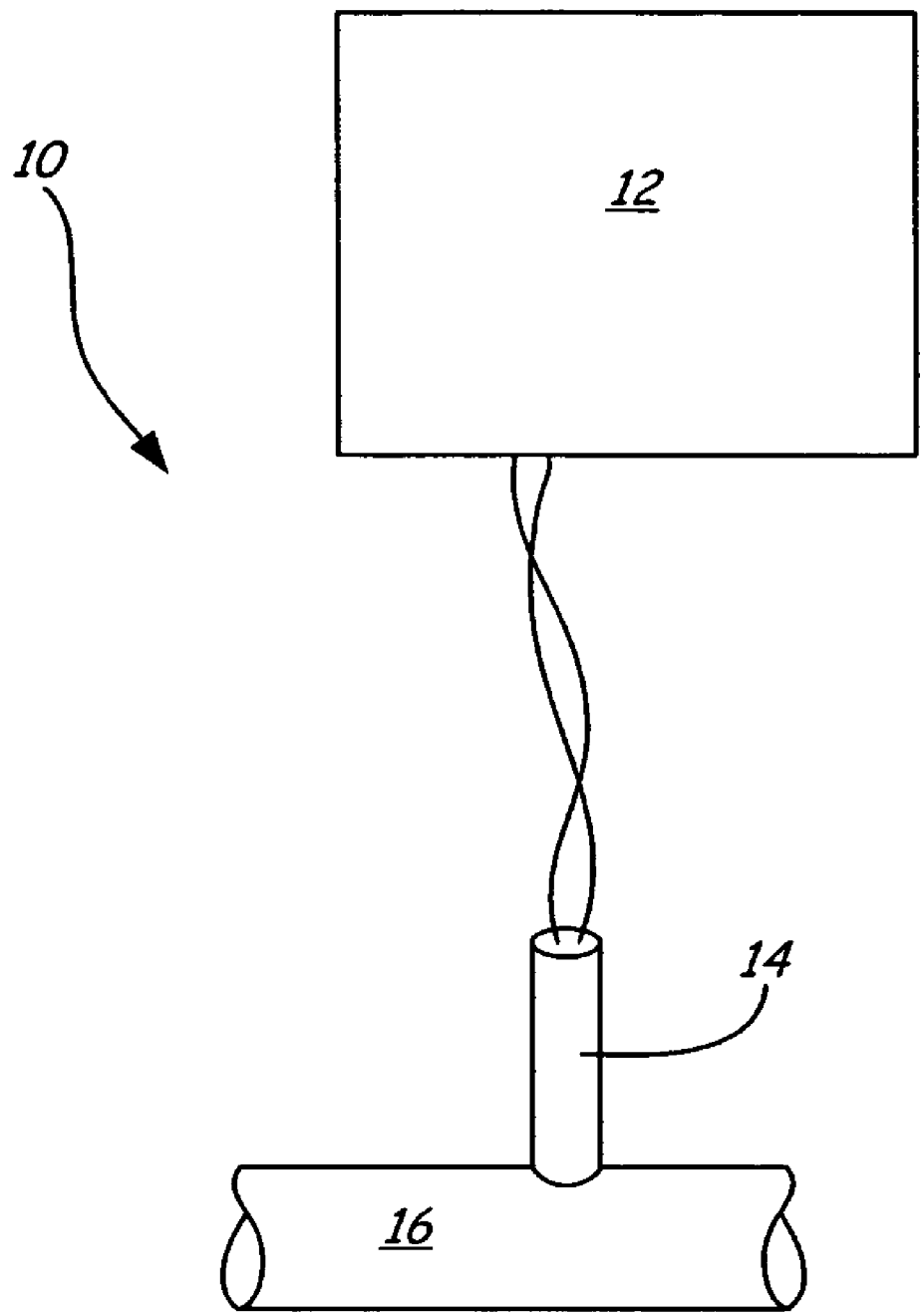
FIG. 2 is a diagrammatic view of a free chlorine monitoring system in which embodiments of the present invention are particularly useful.

FIG. 2 is a diagrammatic view of a free chlorine monitoring system in which embodiments of the present invention are particularly useful. System 10 includes analysis device 12 and sensor 14. Analysis device 12 can be any suitable device capable of generating meaningful free chlorine information from sensor 14. For example, device 12 can be an analyzer such as the Model 1054 Microprocessor Analyzer available from Rosemount Analytical Inc. Uniloc Division of Emerson Process Management. Device 12 can also be a transmitter that is adapted to generate chlorine data and transmit the data over a process communication loop. One example of such a transmitter is the Model 1181RC Transmitter available from Rosemount Analytical Uniloc. Sensor 14 is coupled to liquid sample specimen container 16, which may be a pipe, for example. Sensor 14 has an electrical characteristic that varies in response to free chlorine concentration in the liquid specimen.

Figure 3:
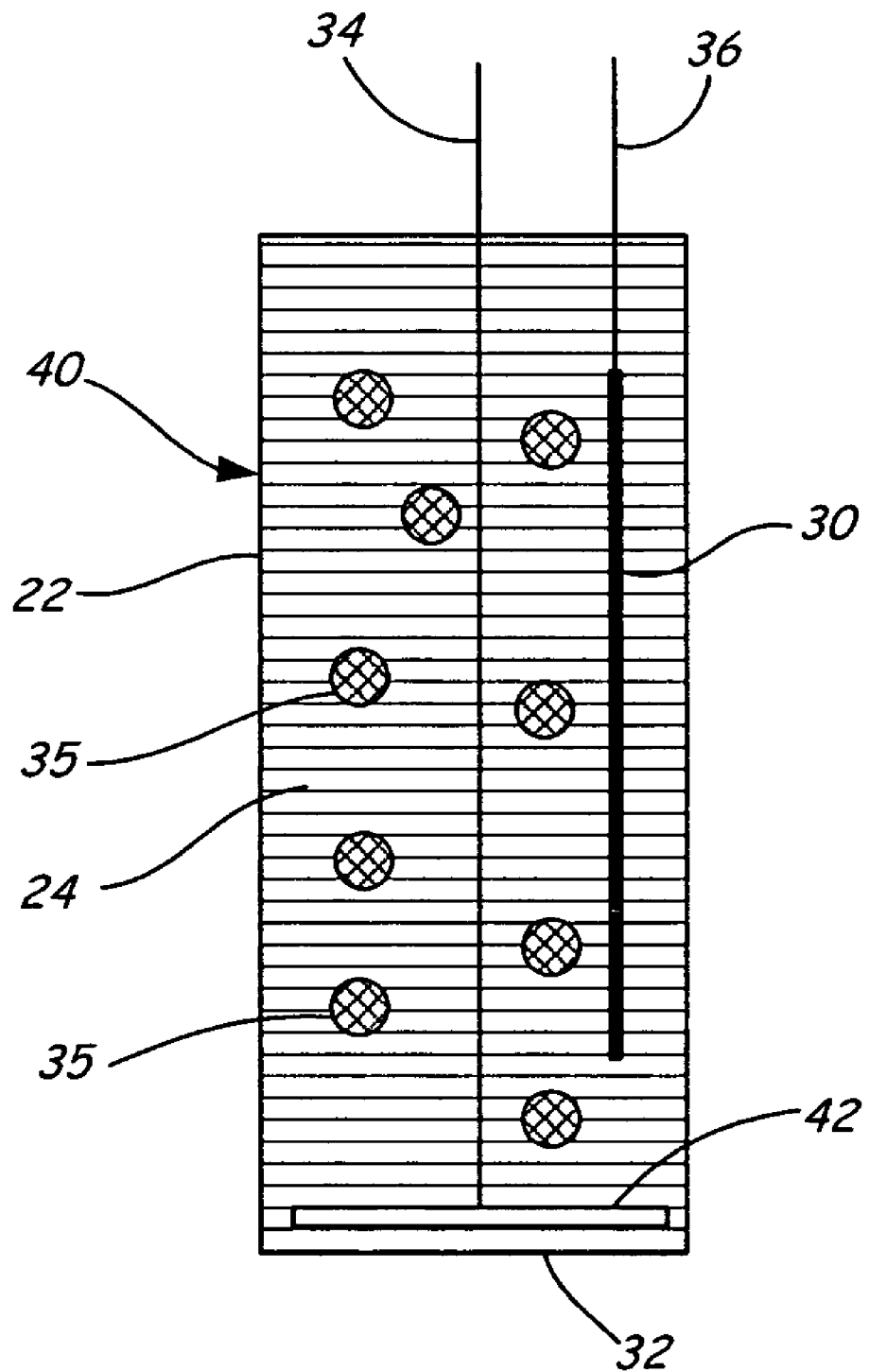
FIG. 3 is a diagrammatic view of a free chlorine amperometric sensor in accordance with an embodiment of the invention.

FIG. 3 is a diagrammatic view of a free chlorine amperometric sensor 40 in accordance with an embodiment of the invention. Working electrode 42 is disposed proximate porous, hydrophilic membrane 32. In one preferred embodiment, working electrode 42 is a Gas Diffusion Electrode (GDE). In this example, electrode 42 is a GDE loaded with 80 percent platinum-black (powdered platinum) and carbon on a carbon cloth electrode (ECC). The platinum was distributed at a density of about 5.0 mg/cm$^2$. The configuration used for working electrode 42 can be obtained from E-Tek, Inc. (www.etek-inc.com), of Somerset, N.J., USA, by specifying the loading and density listed above. Although FIG. 3 shows working electrode 42 as a GDE, other forms of porous electrodes, such as a mesh, can be used.

One important design consideration for a sensor of this type is the rate at which the electrolyte is lost. Specifically, since the hydrophilic membrane is porous, there will be a loss of the electrolyte over time, and if the rate of the loss is believed to be generally unacceptable, the sensor will need to be frequently refilled. In order to limit the rate of loss, a long-term pH stabilizer is used as the electrolyte. The long-term pH stabilizer is generally in the solid form of a weak acid or base 35 that is provided in the electrolyte solution to maintain the pH at a selected level according to its dissociation constant. To achieve an acceptable rate of loss, it is desirable for the acid or base to have a solubility in water, at room temperature (about 25 degrees Celsius), between about 1.2 M/liter and about 0.001 Moles/liter. Exemplary acids with suitable solubility are succinic acid (butanedioic acid); adipic acid (hexanedioic acid); suberic acid (octanedioic acid); and boric acid. The low solubility acid is used to maintain the electrolyte at a low concentration. If desired, the pH can instead be maintained at a relatively high level by employing a base with a suitably low solubility, again between about 1.2 M/liter and about 0.001 M/liter in water at room temperature. To reduce the refill frequency, solid phase of the acid or base is stored inside the sensor chamber as shown in FIG. 3. As the dissolved acid or base is lost through the hydrophilic membrane, the solid phase will continue to supply the acid or base to keep the solution saturated for a long time.

Figure 4:
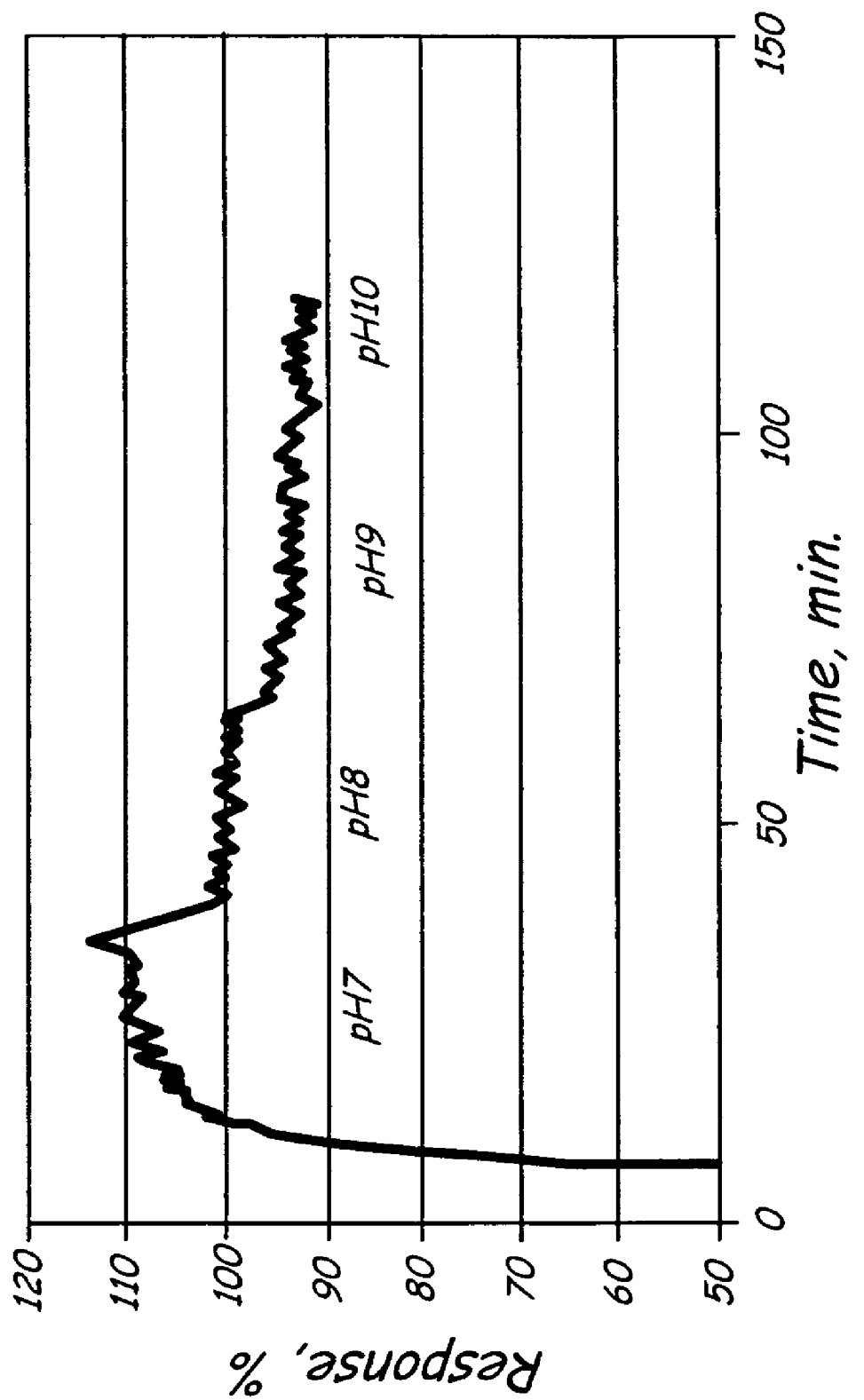
FIG. 4 is a graph of sensor response for a free chlorine sensor in accordance with an embodiment of the present invention.
Figure 5:
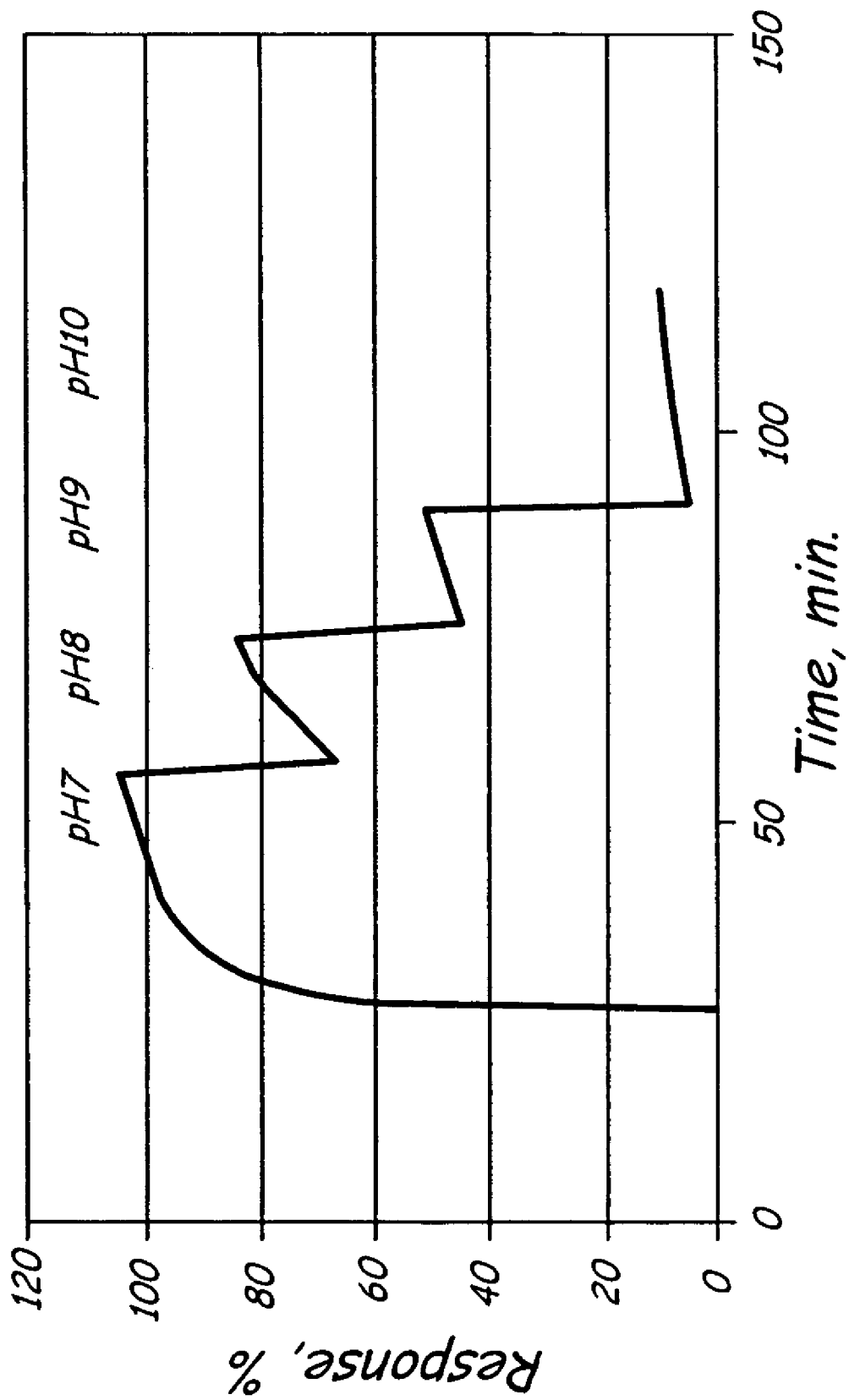
FIG. 5 is a graph of sensor response for a free chlorine sensor in accordance with the prior art.

FIGS. 4 and 5 illustrate the contrast of sensor response for a sensor in accordance with the present invention (FIG. 4) and a sensor in accordance with the current state of the art (FIG. 5). As illustrated sensor response for prior art sensor vary dramatically as pH goes from 7 to about 10. On the other hand, the sensor response shown in FIG. 4, while showing minor pH dependence is not nearly as dramatic as that of FIG. 5. In fact, it is believed that the effect of varying specimen pH will have such little effect on the response of sensors in accordance with the present invention, that pH measurement and compensation can be eliminated. Further, the provision of long-term pH control within the electrolyte fill solution is done simply by virtue of the selection of a suitable acid or base.

Although the present invention has been described with reference to present embodiments, workers skilled in the art will recognize that changes may be made in form and detail without departing from the spirit and scope of the invention.

What is claimed is:

1. An amperometric sensor for measuring free chlorine in a solution, the free chlorine being in the form of hypochlorite ion and hypoclorus acid, the sensor comprising:
   a sensor body;
   an electrolyte disposed within the sensor body;
   a membrane coupled to the sensor body and adapted to pass hypochlorite ion and hypoclorus acid therethrough into the sensor body;
   a reference electrode disposed in the electrolyte;
   a porous working electrode disposed proximate the membrane, the porous working electrode being constructed from a noble metal; and
   a solid phase long-term pH stabilizer disposed in the electrolyte, the stabilizer being an acid selected from the group consisting of succinic acid, adipic acid, suberic acid and boric acid, having a solubility in water, at about 25 degrees Celsius, between about 1.2 Moles/liter and about 0.001 Moles/liter, the stabilizer acting to maintain the pH in the electrolyte at a level to cause substantially all hypochlorite ion passing through the membrane to become hypoclorus acid.

2. The sensor of claim 1, wherein the non-compact form is a Gas Diffusion Electrode.

3. The sensor of claim 2, wherein the Gas Diffusion Electrode is loaded with the noble metal in a powdered form.

4. The sensor of claim 3, wherein the noble metal is platinum.

5. The sensor of claim 4, wherein the platinum is loaded onto the Gas Diffusion Electrode at approximately 80% Pt/C.

6. The sensor of claim 2, wherein the Gas Diffusion Electrode includes a carbon cloth.

7. The sensor of claim 1, wherein the non-compact form of the working electrode is a mesh.

8. The sensor of claim 7, wherein the working electrode is constructed from gold mesh.

9. The sensor of claim 1, wherein the membrane is hydrophilic.

10. A system for monitoring free chlorine concentration in a solution, the free chlorine being in the form of hypochlorite ion and hypoclorus acid, the system comprising:
    a free chlorine amperometric sensor including:
      a sensor body;
      an electrolyte disposed within the sensor body;
      a membrane coupled to the sensor body and adapted to pass hypochlorite ion and hypoclorus acid therethrough into the sensor body;
      a reference electrode disposed in the electrolyte;
      a porous working electrode disposed proximate the membrane, the porous working electrode being constructed from a noble; and
      a solid phase long-term pH stabilizer disposed in the electrolyte, the stabilizer being an acid selected from the group consisting of succinic acid, adipic acid, suberic acid and boric acid, having a solubility in water, at about 25 degrees Celsius, between about 1.2 Moles/liter and about 0.001 Moles/liter, the stabilizer actin to maintain the pH in the electrolyte at a level to cause substantially all hypochlorite ion passing through the membrane to become hypoclorus acid; and
    an analysis device coupled to the reference electrode and the working electrode, the analysis device adapted to provide a sufficient working potential and to measure a current flowing between the reference electrode and working electrode and provide an indication of free chlorine concentration based on the current.

11. The system of claim 10, wherein the analysis device is a transmitter.

* * * * *